United States Patent
Herzog et al.

(10) Patent No.: US 10,786,293 B2
(45) Date of Patent: Sep. 29, 2020

(54) MANDIBULAR RESECTION TEMPLATE

(71) Applicant: KARL LEIBINGER MEDIZINTECHNIK GMBH & Co. KG, Mühlheim (DE)

(72) Inventors: Rebecca Herzog, Mühlheim (DE); Lorenz Gabele, Mühlheim (DE)

(73) Assignee: Karl Leibinger Medizintechnik GmbH & Co. KG, Muehlheim (DE)

( * ) Notice: Subject to any disclaimer, the term of this patent is extended or adjusted under 35 U.S.C. 154(b) by 148 days.

(21) Appl. No.: 16/090,764

(22) PCT Filed: May 2, 2017

(86) PCT No.: PCT/EP2017/060433
§ 371 (c)(1),
(2) Date: Oct. 2, 2018

(87) PCT Pub. No.: WO2017/191140
PCT Pub. Date: Nov. 9, 2017

(65) Prior Publication Data
US 2020/0222060 A1    Jul. 16, 2020

(30) Foreign Application Priority Data
May 6, 2016   (DE) .................. 10 2016 108 433

(51) Int. Cl.
*A61B 17/80*    (2006.01)

(52) U.S. Cl.
CPC ............................ *A61B 17/8071* (2013.01)

(58) Field of Classification Search
CPC . A61B 17/80; A61B 17/8004; A61B 17/8009; A61B 17/8061; A61B 17/8071
See application file for complete search history.

(56) References Cited

U.S. PATENT DOCUMENTS 5,364,396 A * 11/1994 Robinson ............. A61B 17/663
                                                         606/105
5,683,397 A    11/1997 Vendrely et al.
(Continued)

FOREIGN PATENT DOCUMENTS

CN    204863356 U    12/2015
DE    69636636 T2    8/2007
(Continued)

OTHER PUBLICATIONS

International Search Report and Written Opinion, PCT/EP2017/060433, dated Jul. 26, 2017 (in German) (14 pp.).
(Continued)

*Primary Examiner* — Eric S Gibson
(74) *Attorney, Agent, or Firm* — Eversheds Sutherland (US) LLP

(57) ABSTRACT

The present invention relates to a mandibular resection template including a central component which is prepared for attachment to a segment, for example a symphysis segment of a jawbone, such as a mandible or maxilla. At least two separating tool guide portions are present at the central component, a positioning aid being provided between the two or more separating tool guide portions in order to obtain a spatially correct orientation of the mandibular resection template with respect to the jawbone.

10 Claims, 14 Drawing Sheets

(56) References Cited

U.S. PATENT DOCUMENTS

| | | | | |
|---|---|---|---|---|
| 6,053,919 A * | 4/2000 | Talos | A61B 17/8071 | 606/300 |
| 6,139,316 A * | 10/2000 | Sachdeva | A61B 17/663 | 433/7 |
| 6,978,188 B1 * | 12/2005 | Christensen | A61B 17/8863 | 700/118 |
| 7,182,785 B2 * | 2/2007 | Elsalanty | A61B 17/8004 | 606/915 |
| 7,998,216 B2 * | 8/2011 | Elsalanty | A61B 17/8004 | 606/282 |
| 8,287,573 B2 * | 10/2012 | Mulone | A61B 17/663 | 606/105 |
| 8,377,105 B2 * | 2/2013 | Buscher | A61B 17/151 | 606/286 |
| 8,808,290 B2 * | 8/2014 | Dubois | A61B 17/663 | 606/58 |
| 9,066,733 B2 * | 6/2015 | Furrer | A61B 17/8061 | |
| 9,381,072 B2 * | 7/2016 | Furrer | A61C 8/0031 | |
| 9,867,638 B2 * | 1/2018 | Vicatos | A61B 17/663 | |
| 10,595,942 B2 * | 3/2020 | Rueber | G06F 30/00 | |
| 10,610,299 B2 * | 4/2020 | Rueber | G06F 30/00 | |
| 2005/0203628 A1 * | 9/2005 | Elsalanty | A61B 17/8004 | 623/17.17 |
| 2007/0276502 A1 * | 11/2007 | Elsalanty | A61B 17/8071 | 623/17.17 |
| 2010/0106197 A1 * | 4/2010 | Buscher | A61B 17/151 | 606/286 |
| 2010/0152734 A1 * | 6/2010 | Mulone | A61B 17/663 | 606/60 |
| 2011/0269100 A1 * | 11/2011 | Furrer | A61B 17/8085 | 433/72 |
| 2011/0301609 A1 * | 12/2011 | Longepied | A61B 17/8085 | 606/71 |
| 2012/0029574 A1 * | 2/2012 | Furrer | A61B 17/151 | 606/280 |
| 2012/0029646 A1 | 2/2012 | Fernandes | | |
| 2012/0316561 A1 * | 12/2012 | Dubois | A61B 17/663 | 606/58 |
| 2013/0090695 A1 * | 4/2013 | Bernstein | A61B 17/80 | 606/281 |
| 2013/0304075 A1 * | 11/2013 | Tseng | A61B 17/15 | 606/102 |
| 2013/0338779 A1 | 12/2013 | Fernandes | | |
| 2014/0074438 A1 * | 3/2014 | Furrer | A61B 17/8071 | 703/1 |
| 2015/0051876 A1 * | 2/2015 | Rueber | G06F 30/00 | 703/1 |
| 2015/0265378 A1 * | 9/2015 | Furrer | A61B 17/8061 | 700/118 |
| 2016/0331427 A1 * | 11/2016 | Waizenegger | A61B 17/1728 | |
| 2017/0296242 A9 * | 10/2017 | Waizenegger | A61B 17/176 | |
| 2018/0055573 A1 * | 3/2018 | Rueber | A61B 17/80 | |
| 2018/0103965 A1 * | 4/2018 | Waizenegger | A61B 17/8071 | |
| 2018/0116700 A1 * | 5/2018 | Johnston, Jr. | A61B 17/8085 | |
| 2019/0076154 A1 * | 3/2019 | Herzog | A61B 17/15 | |
| 2019/0357952 A1 * | 11/2019 | Waizenegger | A61B 17/1728 | |

FOREIGN PATENT DOCUMENTS

| | | | |
|---|---|---|---|
| EP | 2792329 A2 | 10/2014 | |
| EP | 3000439 A1 | 3/2016 | |
| GB | 2324470 A | 10/1998 | |
| JP | 2018023835 A * | 2/2018 | A61B 17/8061 |
| JP | 2019122784 A * | 7/2019 | A61C 8/0031 |
| WO | 2004039266 A1 | 5/2004 | |
| WO | 2015081027 A1 | 6/2015 | |

OTHER PUBLICATIONS

Office Action, DE 10 2016 108 433.6, dated Dec. 12, 2016 (8 pp.).

* cited by examiner

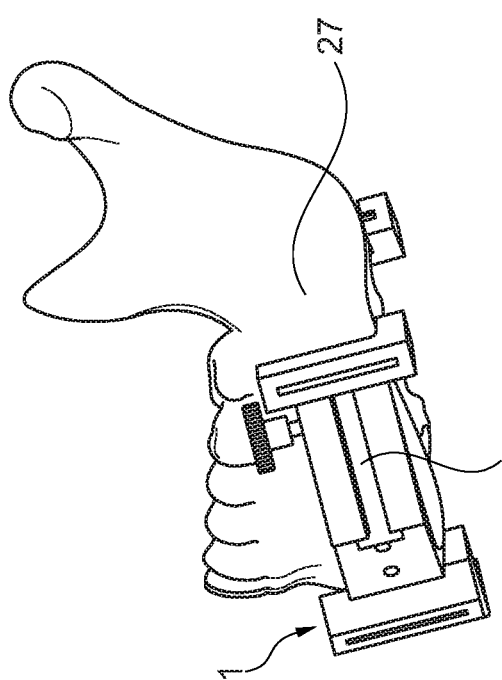
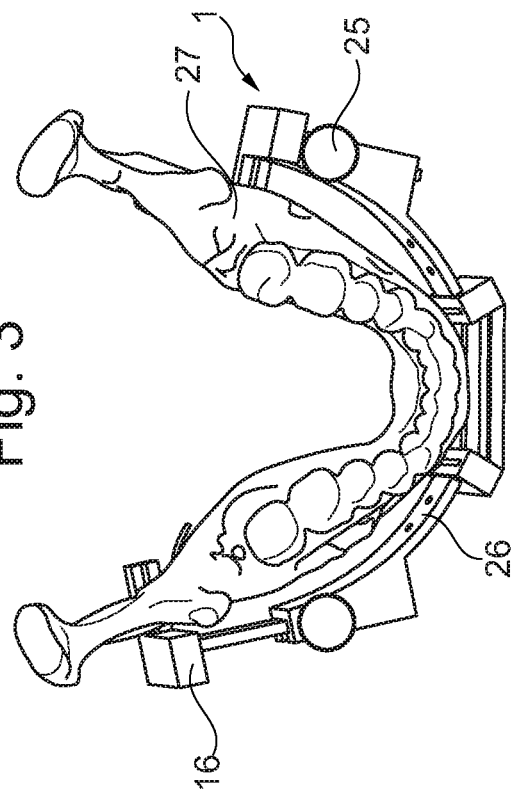
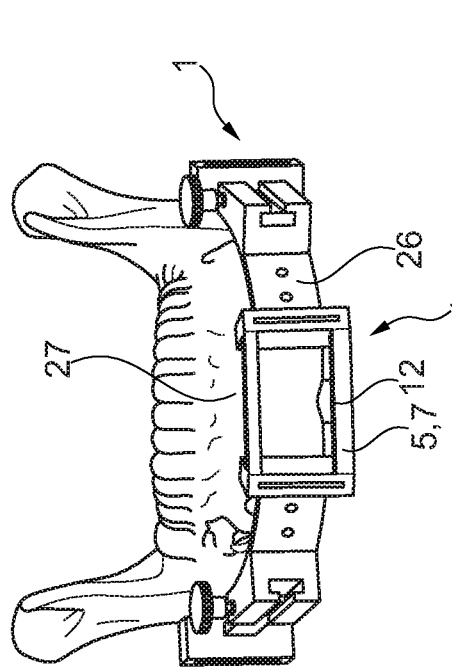
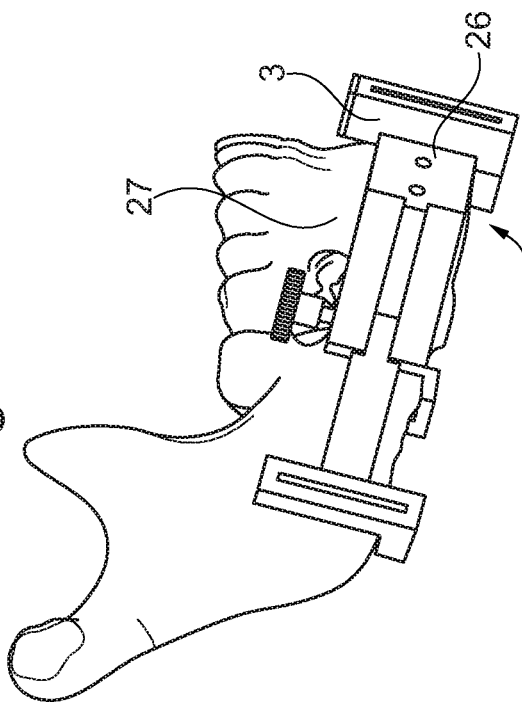

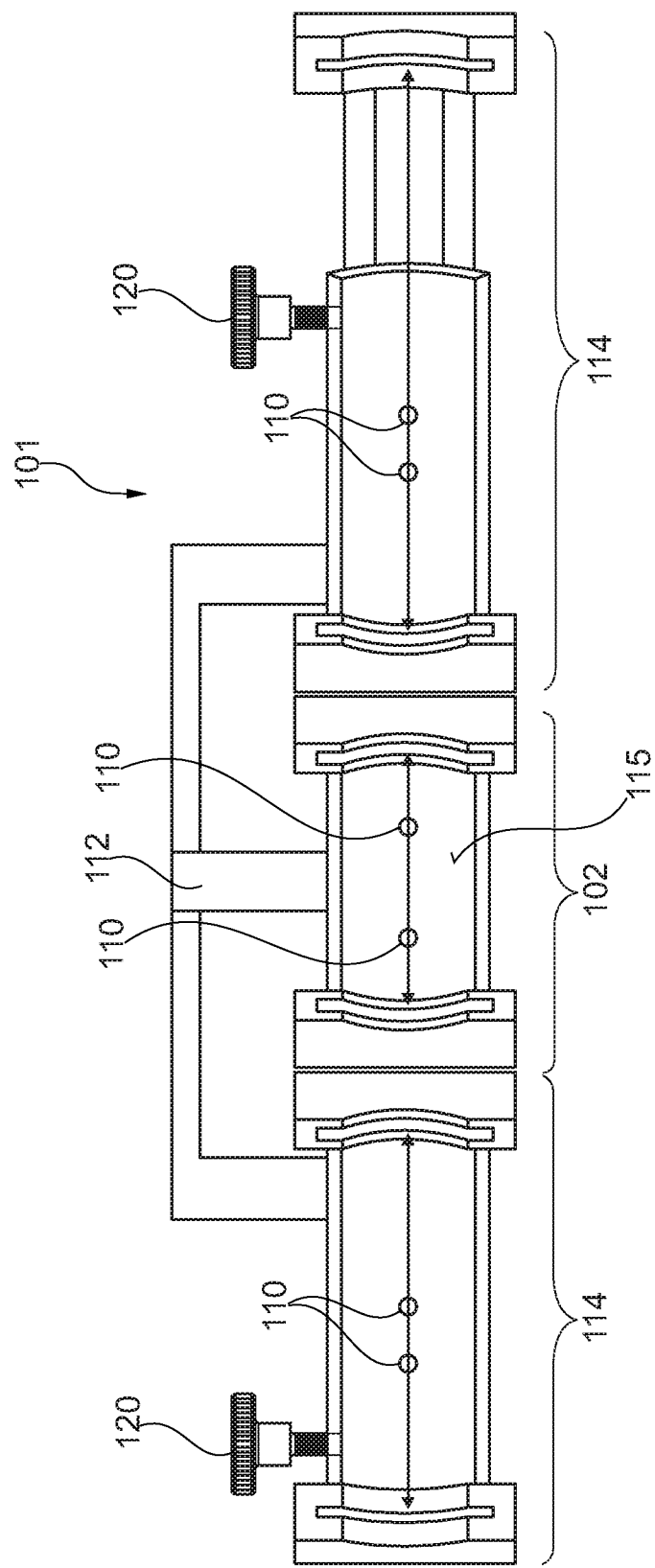

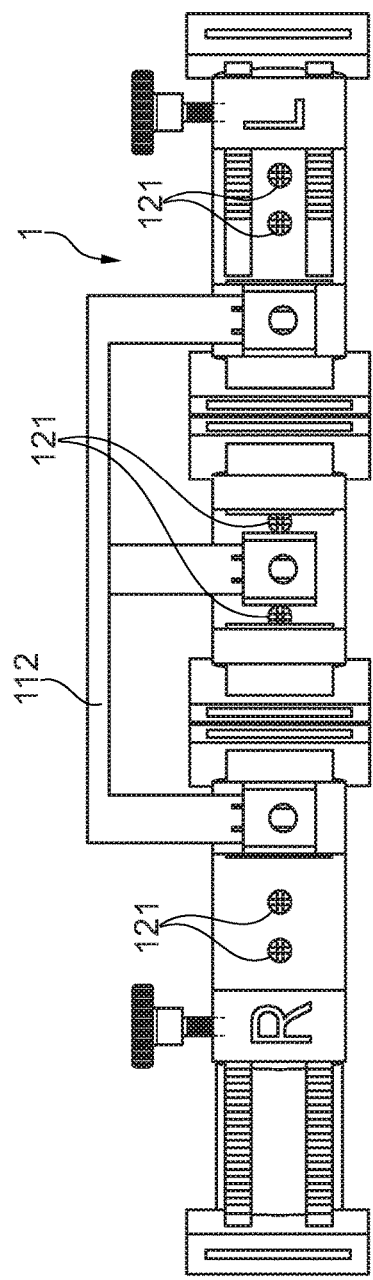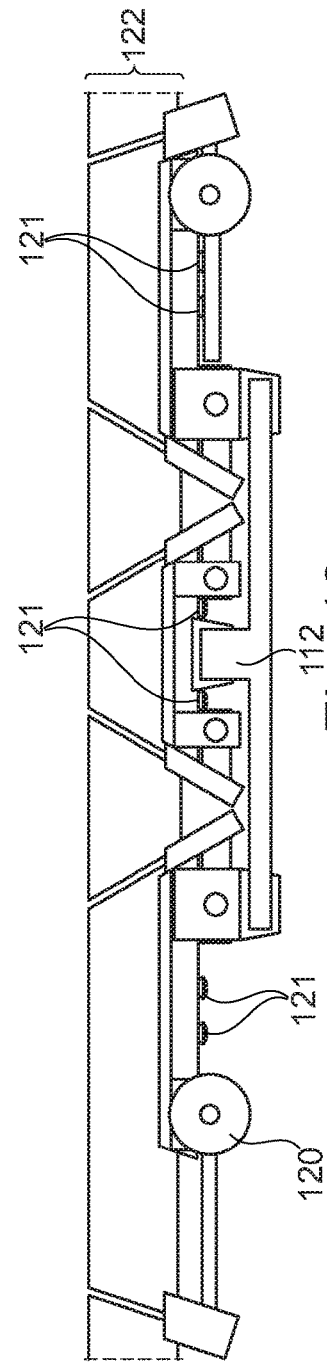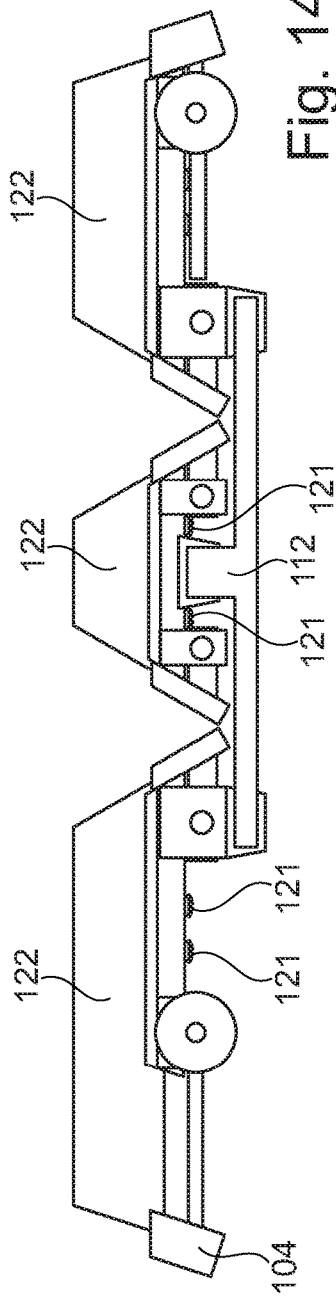

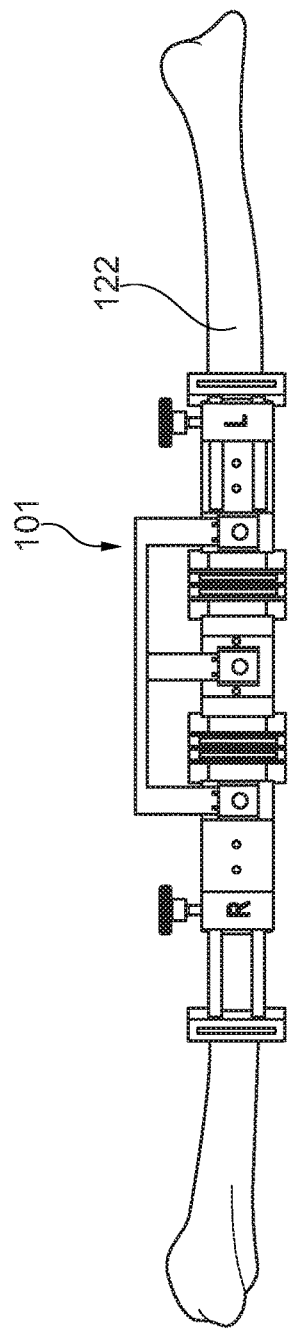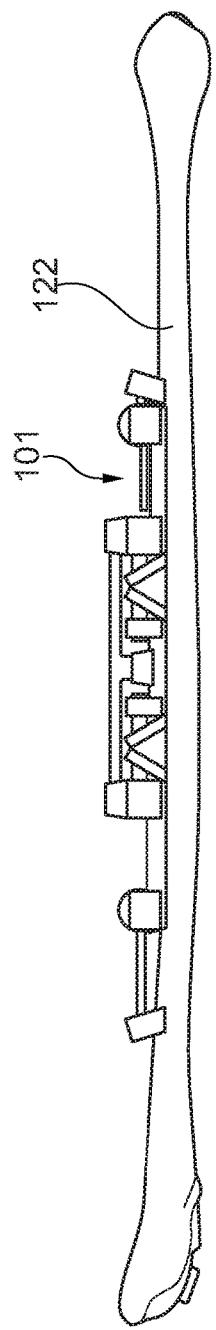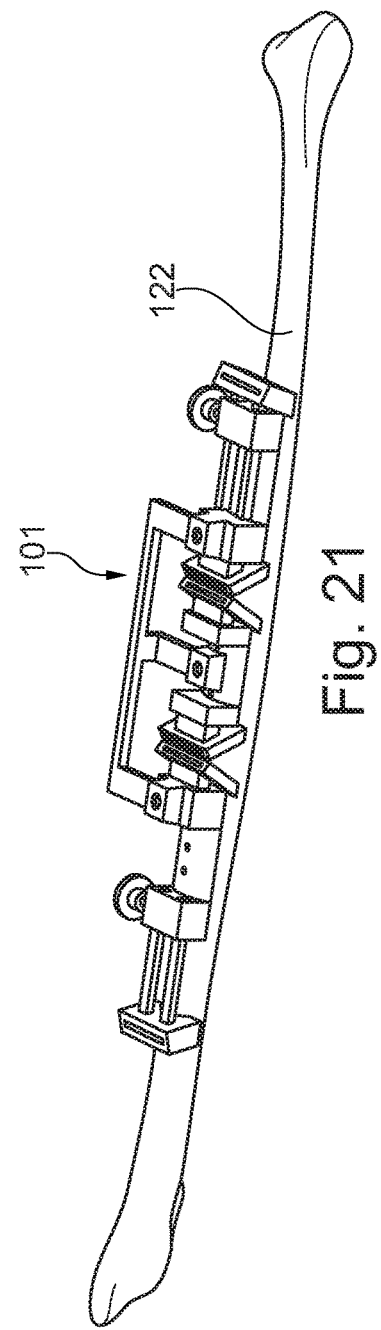

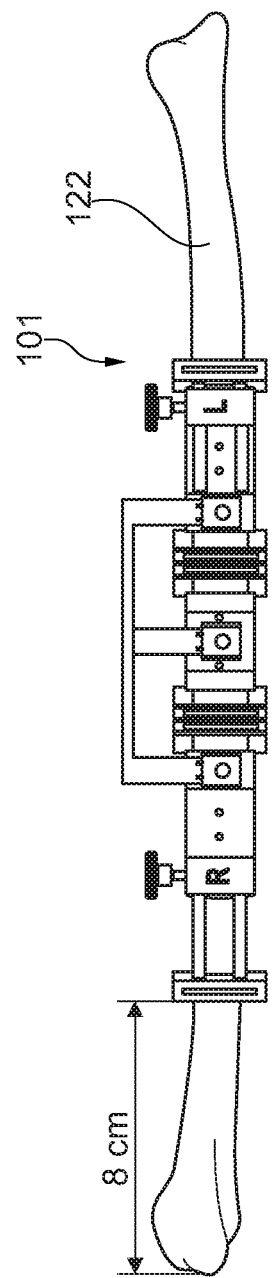
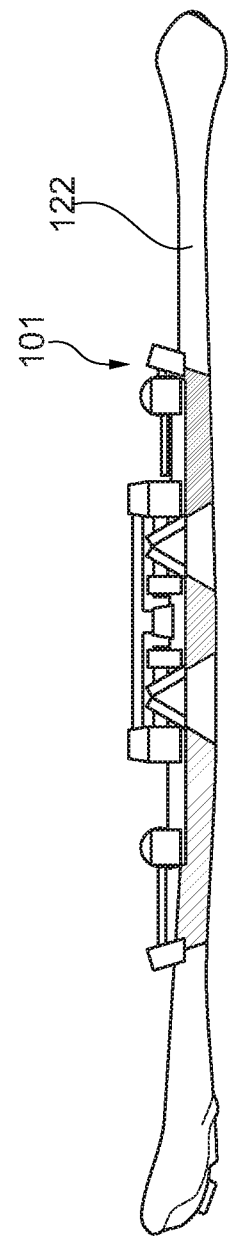
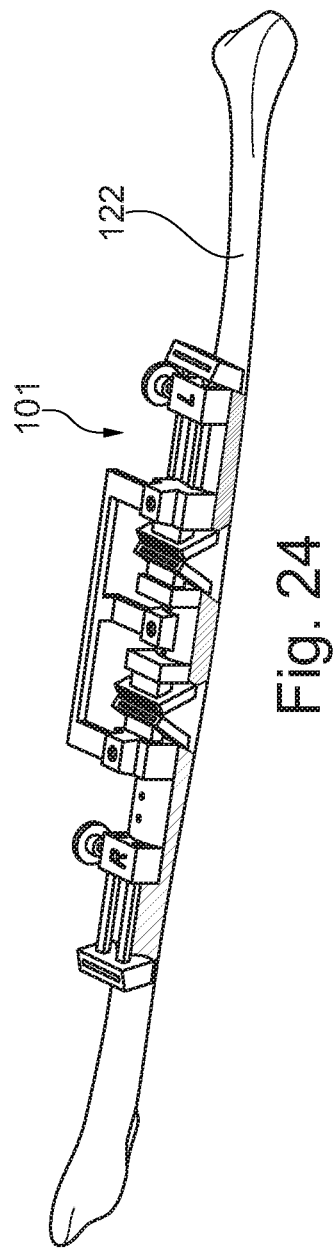

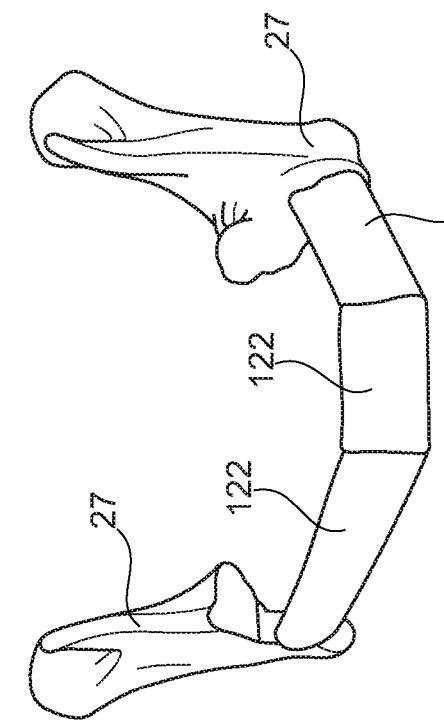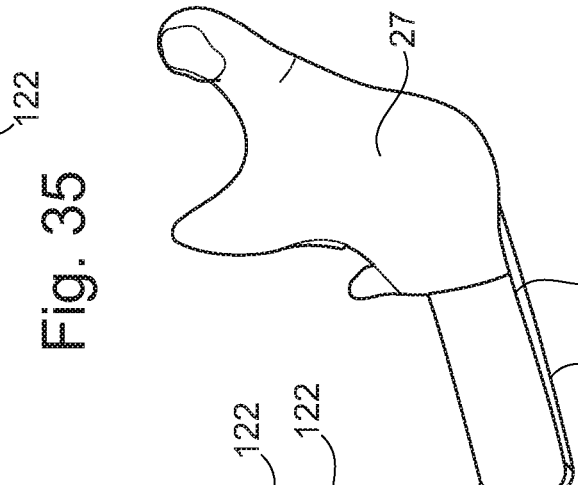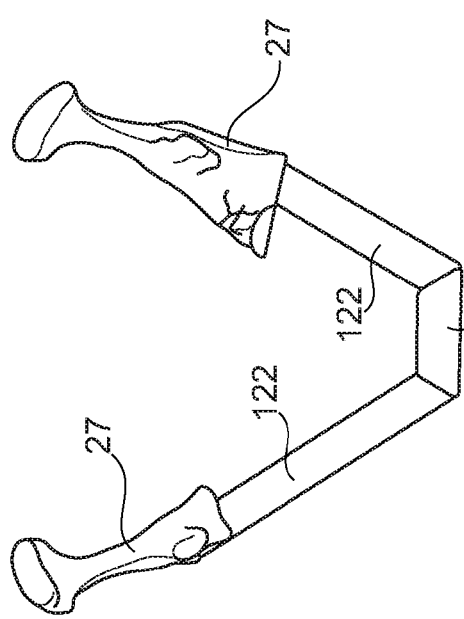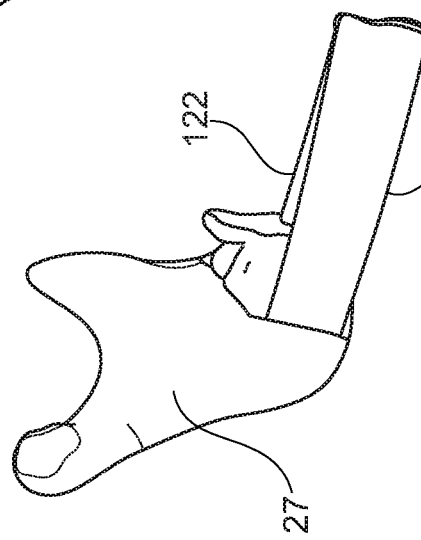

MANDIBULAR RESECTION TEMPLATE

TECHNICAL FIELD

The invention relates to a mandibular resection template comprising a central component which is prepared for attachment to a segment, for example a symphysis segment of a jawbone, such as a mandible or maxilla, wherein at least two separating tool guide portions are present at the central component.

BACKGROUND OF THE INVENTION

From the state of the art already sawing templates such as mandibular resection templates are known. For example, WO 2004/039266 A1 discloses a sawing template that can be used at a fibula or a mandible. Similar devices are also known from US 2012/0029646 A1, US 2013/0338779 A1 and US 2013/0304075 A1.

Human mandibular bones, for example, such as a mandible may happen to be damaged by an accident or by carcinogenic changes so that parts of said bone have to be resected. After that, the bone has to be re-completed. Recently, one has turned to insert bone portions which were resected e.g. from a fibula, viz. a calf bone, at the position freed from defects/cavity of the mandible. For this purpose, it is necessary to carry out precise cuts in a predetermined manner both on the mandibular bone and then correspondingly at the fibula.

To this end, usually mandibular resection templates are employed which thus are in charge of a precise separating guide at the mandible, just as fibula bone material resection and transfer templates which are in charge of precise cuts at the fibula and, at the same time, are used for precise transfer of the cut-out bones for being implanted in the jaw area.

The previously known solutions are not sufficiently precise although they are very complicated to handle. Moreover, they are relatively cost-intensive. In this respect, an improvement is to be achieved.

SUMMARY OF THE INVENTION

Hence, it is the object of the present invention to eliminate or at least alleviate the drawbacks from the state of the art and to make available a low-cost mandibular resection template which can be used in cooperation with a fibular bone material resection and transfer template so that an esthetically and mechanically appealing result can be achieved in the mandibular area.

In single cases, for mandibles a particular patient-specific template is manufactured. This is very cost-intensive and time-consuming, however, therefore the approach of the present invention resides in providing a universal mandibular resection template which is finally adapted to a representative patient out of the variety of all potential patients.

Especially universal templates for resection of the mandibula and the fibula for upcoming mandibular reconstruction of the microvascular fibula transplant as well as a system of mini-plates for fixation of the transplant adapted to said technology are to be made available.

This object is achieved in a generic device by the fact that between the two or more separating tool guide portions, such as in the form of saw blade guide portions, a positioning aid is present so as to obtain a spatially correct orientation of the mandibular resection template with respect to the jawbone. In this way, the mandibular resection template can be fastened more exactly and easily than previously to the cranial bone, especially to a jawbone, preferably to the mandibular bone of the specific patient so that a highly precise resection of the bone portions to be removed can be carried out.

Within in the framework of the project according to the invention, universal templates for resection of the mandibula and of the fibula were developed. It was not only intended to obtain a clear simplification and standardization of the clinical intervention of the mandibular reconstruction by means of the microvascular fibula transplant but also to enforce saving of cost and time as compared to patient-specific resection templates. This was achieved by the configuration according to the invention.

In addition, concerning the resection templates also a plate system configuration for transplant fixation adapted to this technology has been worked out. In contrast to the current state of science according to which reconstruction plates are used for bridging a defect or for fixing the transplant, now substantially thinner mini-plates having a profile thickness of 1 mm (1.0 mm) are used, as they entail a significant advantage in material removal according to the experience gained.

Plates such as reconstruction plates (larger than 1.0 mm in thickness up to about 3.0 mm) or mini-plates (smaller than or equal to 1.0 mm in thickness) which may have a lattice design, are adapted to the average shape of the mandibula and, resp., are pre-shaped to the fibula transplant resulting from the saw cut of the resection template. In this way, high fitting accuracy is achieved and the transplant fixation is significantly facilitated.

What is definitely important is the fact that the mandibular resection template is adapted to the average shape of the mandibula. The resection template is as flexible as possible in its setting so as to cover a plurality of different resection patterns, at any rate the following cases, however: triple-segment resection (right-hand mandibular body—front segment—left-hand mandibular body), double-segment resection (right-hand mandibular body including front segment), double-segment resection (left-hand mandibular body including front segment) and single-segment resection. In this way, about 80% of all the theoretically possible resections are covered.

In the rear area of the resection template, an adaptation of length is made possible which enables the saw slit to be displaced depending on the extent of the defect. The flexible saw slit is locked by a basally arranged set screw. The set screw preferably is not removable so as to facilitate handling and to reduce the risk of accident/loss. However, concerning the conditioning of the resection template it is advantageous when the single parts can be easily dismounted and/or the gaps occurring are so large that medium used for disinfection may have a simple and efficient cleaning effect.

For carrying out the resection an oscillating saw is used. It is being considered to design the saw slit to be approx. 1 mm in width (+/−0.1 to 0.2 mm) and open to the bottom and/or to the top. A lateral guide of the saw blade is predetermined in any case.

The resection template is primarily intended to be attached to the mandible in one piece. In addition to that, then only individual segments are enabled to be attached to the mandible. Via a plug mechanism or a similar connecting constellation the front segment including the right side or the front segment including the left side are kept to be separable from the remainder.

Integrated bores enable the template to be fixed to the mandible by means of standard screws having e.g. a diameter of 2.0 mm.

An attached center line marker in the front segment has an advantageous effect on the orientation and the exact alignment of the resection template on the mandible. Exact positioning is facilitated.

All removable components of the resection template will additionally obtain side markers such as e.g. "R" for the right and "L" for the left. A tumor resection or resection of the mandible is carried out according to anatomic regions (right-hand mandibular body, symphysis, left-hand mandibular body), i.e. when the tumor is located e.g. in the center of the mandibular body, resection will take place up to the mandibular angle and to the symphysis region.

Advantageous embodiments are claimed in the subclaims and shall be illustrated in detail hereinafter.

It is of advantage when the positioning aid is in the form of a notch and bead combination, a notch, a bore, a prism, a color marker, a pin, a screw or a navigation positioning and/or is configured as a positioning fin prepared for contacting a portion of the mandibular bone, such as the symphysis segment.

It is also advantageous when the positioning aid and, resp., the positioning fin projects transversely, preferably orthogonally from the central component. Thus, the orientation of the mandibular resection template is facilitated.

It is useful when the central component is in the form of a frame. Then the view onto the mandible is improved.

The handling is improved when the frame has two horizontal webs which are preferably connected to each other at the distal ends thereof via the two saw blade guide portions.

A particular exemplary embodiment is characterized in that the two separating tool guide portions/saw blade guide portions and the two horizontal webs take a rectangular shape at least in a frontal projection. Then the assembly of the individual components is facilitated.

It is also advantageous when the two horizontal webs and the two separating tool guide portions/saw blade guide portions are in the form of a uniform and/or one-piece/integral and/or single-material component or at least one of the separating tool guide portions/saw blade guide portions or both separating tool guide portions/saw blade guide portions is/are a respective part of a displacing component detachable/displaceable/separate from the horizontal webs.

When at least one of the separating tool guide portions/saw blade guide portions has a saw slit dimensioned for guiding a bone separating tool, such as a saw blade/a circular saw, the bone separating tool is prevented from running untrue or tilting.

An especially efficient guide is achieved when on both sides of the saw slit a bone separating tool contact face parallel to the latter is formed.

Accordingly, it is of advantage when the saw slit completely protrudes through the material forming the same and, in addition, is configured in extension of its longitudinal extension to be open on one side or on two sides.

The mandibular resection template is especially resistant to break when the material accommodating the saw slit is block-shaped, preferably equipped with surfaces (almost) orthogonal to each other, and/or one of the horizontal webs takes a rectangular beam shape, with the horizontal webs being formed e.g. geometrically identically.

It is advantageous when in the area of the positioning fin a marker for the positioning aid is present, such as in the form of a center line marker, a (through/blind) hole, a projection, an indentation/recess, a ridge, a groove, a flute or a corrugation. When, for example, a slit is introduced to the mandible, then the ridge can be easily inserted there. By form closure the mandibular resection template then can be precisely aligned. However, also other graphical center line markers are helpful.

It is advantageous when the marker is in the form of a ridge extending along the longitudinal axis of the fin and having points, for example an acute or triangular cross-section. Although in this case drawbacks have to be expected during manufacture, the orientation of the templates relative to the bone is possible in an especially quick and in a non-tiltable manner in such configuration.

The visibility is improved when the marker is present at a front and/or upper side of only one horizontal web or both horizontal webs and/or at the upper side of the positioning fin and/or at the lower side of the central component.

It is worth mentioning that the ridge is present on the upper side of the positioning fin. This allows for efficient handling.

When the positioning fin projects perpendicularly from either of the two horizontal webs, preferably only from the lower one of the two horizontal webs, and preferably also perpendicularly to the two saw slits, e.g. as an integral component of the horizontal web, the mandibular resection template can be properly attached from below.

It has proven itself when an extension component adjoins either or each of the two separating tool guide portions/saw blade guide portions on the side facing away from the central component. The space to be treated then can be extended.

It is helpful in this context when the extension component is an integral part of the central component or is a separate extension component adapted to be detachably coupled to a connecting point.

One advantageous exemplary embodiment is also characterized in that the connecting point makes use of two matching coupling geometries which are positively and/or non-positively interacting.

Especially when the one coupling geometry forms a projection and the other coupling geometry forms a matching recess, quick plugging of the individual components can be brought about.

It has proven itself when the coupling geometries interact in a dovetail manner.

One advantageous exemplary embodiment is also characterized in that the recess is formed as a blind hole open at a partial area along its longitudinal axis.

When a bottom of the blind hole defines a stop for the projection, even in stressful situations precise assembly of the single parts of the mandibular template is facilitated.

Also, the resection can be carried out in an especially efficient manner when a plane extending through the saw slits takes an angle of about 10° to about 20°, preferably about 12°+/−5° with the upper and lower horizontal struts, when measured on a side facing the mandible.

It is of advantage when the extension component has a circular body from which an extra separating tool guide portion/extra saw blade guide portion projects distally, i.e. at a free end, ergo is present on a side distant from the connecting point.

It has proven itself when in the base body at least one through-hole for receiving a bone screw is provided. The mandibular template is prevented from getting out of place during, or before or after, resection.

In order to enforce proper pulling when screwing the bone screw of the resection template to the mandible, it is advantageous when the through-hole extends diagonally, for example is tilted, with respect to the surface of the base body.

In order to further avoid pivoting, it is of advantage when two through-holes are arranged in parallel to the longitudinal axis of the extension component, advantageously offset against an outer edge of the extension component.

Accordingly, it has proven itself that the through-holes are offset toward the lower outer edge. Preferably, the through-holes are arranged in the lower third of the extension component, however.

More exactly speaking, it is thus useful when the through-holes are ascending from "the front" to "the rear". "The front" in this context is the area which is arranged outside of the patient, whereas "the rear" then is provided on the inside of the patient. "At the bottom", just as "at the top", is defined by the gravity.

When a central axis of a through-hole adopts an angle of about 20°+/−5° with the front or rear substantially vertically orientated surface, the template is pulled tightly matching to the bone when the fastening screws are screwed in.

It has proven itself when the extra separating tool guide portion/extra saw blade guide portion can be removed from the base body, for example via a setting mechanism. Thus, the flexibility of use and, resp., the applications are increased.

When the extra saw blade portion has a through-slit between two guide surfaces, even there the precision of the cut to be made can be increased. Preferably, an upper or lower end of the through-slit has to be left open.

It has equally proven itself when the extra saw blade portion includes a rod projecting from a block and being adjustably held in an e.g. open channel or a groove.

It is of advantage when the rod can be fixed within the channel via a locking means such as a screw.

Furthermore, it is advantageous when a mandibular bearing block is present at the extension component.

It is desirable when the mandibular bearing block then projects (almost) perpendicularly from the rear surface of the base body or of the extra saw blade portion.

If a slotted hole the longer transverse axis of which is defined by the longitudinal direction of the mandibular hole is formed in the mandibular frame, easy positioning is enabled while accuracy is still given.

Also, it is of advantage when two extension components are present which are mirror-symmetrical to a center plane, with the center plane being the plane in which the ridge is located and to which the horizontal struts are perpendicular.

One advantageous exemplary embodiment is further characterized in that the central component including its extension components projecting from both ends has such curved shape which (equidistantly) follows the outer contour of an average human mandible.

It is further to be mentioned that, on at least one surface such as the front face, the rod has a corrugation or screening orientated transversely to the longitudinal direction of the rod.

It is of advantage when the mandibular template is (completely) made from metal such as a titanium alloy, or of plastic material such as a polymer. In this context, e.g. stainless steel, titanium alloys and plastic materials such as ABS plastics are imaginable.

In a side aspect, the invention also relates to a fibular bone material resection and transfer template comprising a center part having a central body at each of the ends of which a bone separating tool guide portion is present. Said fibular bone material resection and transfer template is improved, if at least either of the bone separating tool guide portions, preferably both bone separating tool guiding portions, is/are supported so that they can be removed from or pushed close to the center part.

Said fibular bone material resection and transfer template may also be claimed separately from the mandibular resection template, viz. without the features of claim 1.

Said already substantially improved fibular bone material resection and transfer template can also be further improved. Said further improvements shall be illustrated in detail hereinafter.

It is of advantage when the bone separating tool guide portion has a guide slit which is formed between two vertical surfaces and which is open on the front and rear sides thereof. In this way, when resecting bone from the fibula, the bone separating tool is prevented from running untrue. Thus, precise resection is ensured.

It is beneficial to the handling when the guide slit is configured to be open on the lower side or upper side thereof.

The adjustability and flexibility during use/during operation will be improved when a beam which is movably supported in a guide path encompassing the same along its longitudinal direction projects from the bone separating tool guide portion separate from the center part.

It is further useful when a fixing screw designed for securing the beam protrudes into the guide path. Then a simple modification may be carried out intraoperatively or may at least be prepared preoperatively.

It has proven itself when approximately in the middle of the center part a bracket receiving device such as a clip is present into which an auxiliary resection bracket is insertable or inserted. The individual parts of the fibular bone material resection and transfer template then may be fixed to be unchangeable relative to each other in space.

Accordingly, it is of advantage when in the bracket receiving device a hole such as a blind hole or through-hole is present which is prepared for receiving and locking a spring portion fixed to the auxiliary resection bracket. Hence, rapid insertion and removal of the auxiliary resection bracket becomes possible.

It has also proven itself when on both sides of the clip a receiving hole for a bone screw is provided.

For proper attachability it is beneficial when the receiving hole has an axis of symmetry which is orientated transversely, preferably perpendicularly to a central plane receiving the central body.

It is also beneficial to a flexible operative use when on either or each of the two bone separating tool guide portions a supplementary component is provided on the side facing away from the central body. It is of further advantage when at the distal end of the supplementary component a respective further bone separating tool guide portion is arranged to be displaceable and removable from the supplementary component.

An advantageous exemplary embodiment is also characterized in that the bone separating tool guide portions of the supplementary component are identical or at least similar to the bone separating tool guide portions of the central body.

An advantageous exemplary embodiment may also be configured so that two guide webs which are guided in a joint guiding block in separate openings are provided at the bone separating tool guide portion configuration present at the distal free end of the supplementary component.

When in the guiding block one, two or more set screw(s) contacting only the upper guide web is/are inserted, an easily accessible area for locking and releasing the locking can be chosen/used. The set screw preferably is not removable.

It has also proven itself when at one or both guide webs a screening or notch is provided, especially on the front side including ribs which extend transversely, preferably orthogonally to the longitudinal direction of one guide web or of both guide webs. In this case, haptic feedback to the operating surgeon can be relatively easily realized.

It is of advantage when a bracket receiving device for receiving and locking the auxiliary resection bracket is provided at the supplementary component.

An advantageous exemplary embodiment is also characterized in that the bracket receiving device of the supplementary component is configured identically or at least similarly to the bracket receiving device of the central body.

It has further proven itself when the two supplementary components are formed to be mirror-symmetrical to a plane of symmetry penetrated centrally by the central body and vertically by the latter.

It is of advantage when the auxiliary resection bracket has at least two or four (90°) steps. This helps to avoid a deformation of soft tissue.

It is beneficial to the invention when the rear side of the template is prepared for contacting a (human) fibula.

It is desirable when the two guide slits at the central body enclose an angle of about 60°+/−5° and/or the two guide slits of the supplementary component enclose an acute angle such as an angle of about 72°+/−5° in the direction of the rear side.

Accordingly, it is advantageous when the bracket receiving devices are prepared for receiving a rigid/stiff/non-elastic/dimensionally stable (similar to a steel component) auxiliary implanting bracket. In this way, the individual bone pieces can be displaced true to position.

When the auxiliary implanting bracket is identical or similar to the auxiliary resection bracket but differs by the position imposed on the supplementary component and the central body relative to each other, ergo has a configuration geometrically different at the connecting points, transfer of the bones resected from the fibula to the mandible with its respective gaps can be efficiently realized.

Furthermore, it is of advantage when the auxiliary resection bracket forces the supplementary component and the central body into a joint plane, but the auxiliary implanting bracket forces the supplementary component and the central body into a U-shape and/or an orientation consistent with the mandibular contour.

The fibular bone material resection and transfer template can also be referred to as fibula resection template and is adapted to the average shape of the fibula. Hence it is not patient-specific but is adapted to the average patient.

The individual segments and lengths are adapted to the mandibular resection template. The scales of the two templates should be uniformly designed and adapted to each other. However, the preoperative planning need not absolutely be taken into consideration.

The individual segments are connected to each other by a removable bracket. The bracket is intended to be attachable both from the top and from the bottom so as to use the template equally for the right and left fibulae. Moreover, the bracket is to be provided with a small step so that it projects further forward, as this area is frequently obstructed by soft tissue.

The set screws for locking the flexible slits are intended to be arranged preferably orthogonally to the template.

For carrying out the resection an oscillating saw is to be used. It is being considered to design the saw slit to be open or closed about 1.0 mm in width downwards or upwards or on both sides. However, in any case there should be a lateral guidance of the saw blade.

The template is fixed to the fibula by standard screws having an outer diameter of about 2.0 mm. In each segment two bores are located for fixations.

The template should at its best enable fixation of the resected fibula segments by means of implants from the front. At present, each of the right and left segments is connected to the front segment by a plate curved at an angle of about 120°. The plate is arranged from above.

Mini-plates having a profile of 1.0 mm which allow for simple transplant fixation and are pre-shaped up to a three-dimensional shape by way of the average shape of the mandible and, resp., fibula transplant have stood the test. The contour of the average mandible as well as of the fibula is generated on the basis of representative data sets.

The plates have to be made available in different forms and configurations. It is aimed at getting along with as few plates as possible. The exact variants then still have to be established in all. However, four-hole plates including a web and/or six-hole plates including a web are imaginable. The plates should have multi-directional angularly stable plate holes so that they both can be blocking and interact with standard screws. Depending on the necessity, specific instruments may be used to fix the plate, for example screw drivers.

The invention also relates to a method which can be claimed independently of the mandibular resection templates or fibular bone material resection and transfer templates. In this context, it can be claimed that the mandibular resection template is used to resect bone portions at the mandible and/or the fibular bone material resection and transport template is used to resect bone from the fibula and/or by means of the fibula bone material resection and transport template the bones resected from the fibula are transferred to the mandibular area and are implanted there.

As a matter of course, the invention also relates to the combination of the mandibular resection template and the fibular bone material resection and transport template as well as to the use thereof.

BRIEF DESCRIPTION OF THE DRAWINGS

Hereinafter the invention shall be illustrated in detail by way of a drawing in which the different embodiments are shown, wherein:

FIGS. 2 to 5 show the mandibular resection template of FIG. 1 in contact with a mandible in different views (from the front, from the right side, from the left side and from above), each in slight perspective, FIG. 11 shows the fibular bone material resection and transport template from behind, i.e. from the mandibular side, FIG. 12 shows a further fibular bone material resection and transfer template having a low auxiliary resection bracket, FIG. 13 shows a top view onto the fibular bone material resection and transfer template of FIG. 12 in contact with a fibula having already accomplished cuts, FIG. 14 shows the fibular bone material resection and transport template of FIG. 13 with removed residual bone portions, with the bone portions to be transplanted being fastened to the template, FIGS. 19 to 21 show another view of the fibular bone material resection and transfer template according to the invention in contact with a calf bone/fibula in a front view (FIG. 19), a side view (FIG. 20) and in a perspective view (FIG. 21), FIGS. 22 to 24 show another view of the fibular bone material resection and transfer template attached to the fibular bone in plural forms of representation corresponding to FIGS. 19 to 21, with the bones to be resected being shown, FIGS. 34 to 38 show the transplanted bones in the mandibular area in different spatial representations (from above, from the front, in a perspective from the front, in a side perspective on the right and in a side perspective on the left side).

The figures are merely schematic and only serve for the comprehension of the invention. Like elements are provided with like reference numerals. Features of the individual exemplary embodiments may be exchanged for each other.

DETAILED DESCRIPTION

Figure 1:
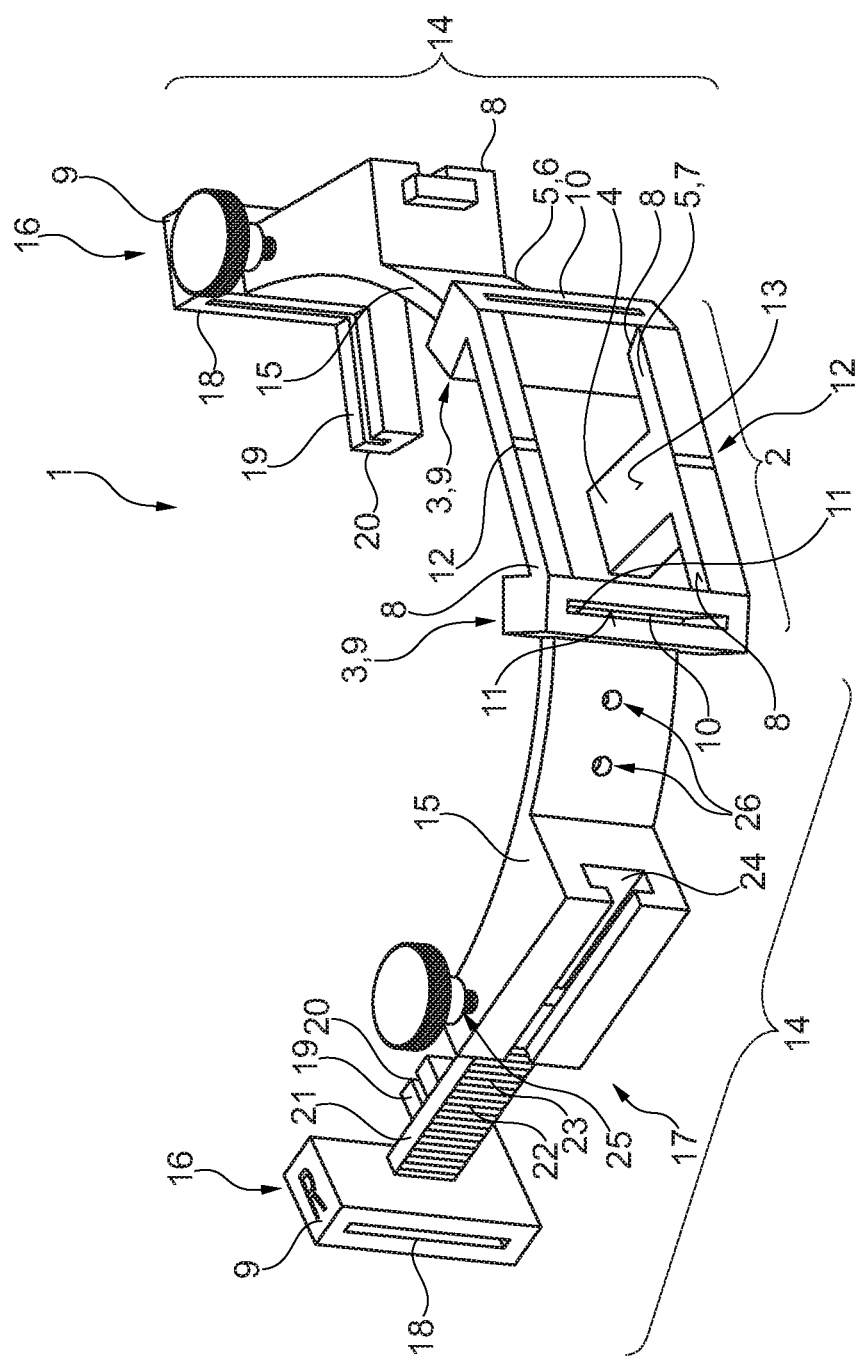
FIG. 1 shows a mandibular resection template according to the invention in a perspective view.
Figure 7:
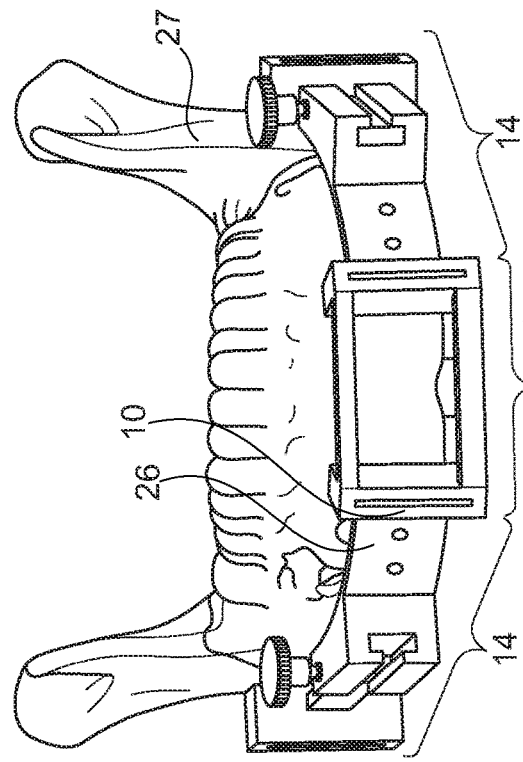
FIGS. 6 to 9 show further representations of different mandibles similar to the representations of FIGS. 2 to 5.
Figure 9:
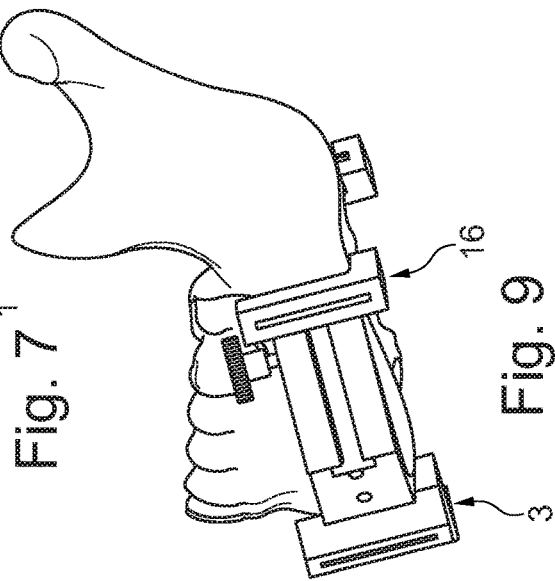
Figure 6:
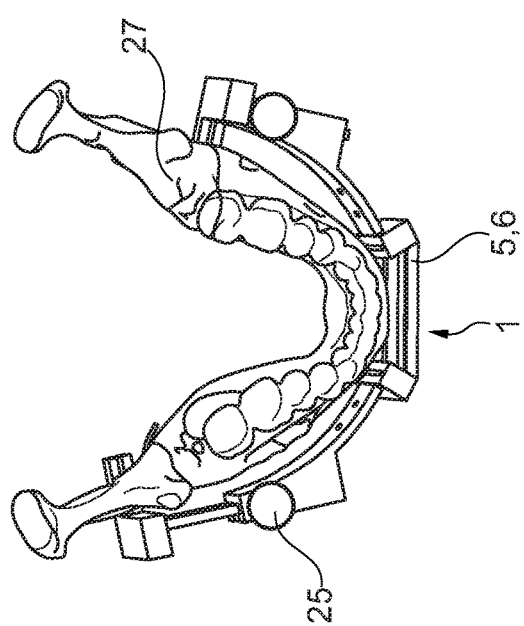
Figure 8:
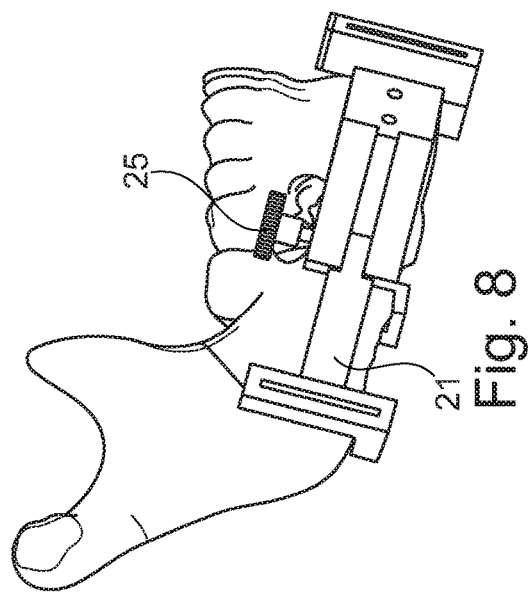

FIG. 1 illustrates a mandibular resection template 1 according to the invention. The mandibular resection template 1 has a central part/central component 2. Said central component 2 is prepared for being transferred to a symphysis segment of a mandible. The central component 2 includes at both outer ends, with the ends defining the longitudinal axis, two separating tool guide portions/cutting tool guide portions/saw blade guide portions 3. Between the two separating tool guide portions/saw blade guide portions 3 a positioning aid/positioning fin 4 is present. The separating tool guide portions need not contact a separating tool, whereas the saw blade guide portions comparable thereto are definitely provided for physically contacting a separating tool such as a milling cutter, a saw blade or any other metallic separating tool. The positioning aid does not necessarily have to enter into physical contact with or even abut on the bone, but may use, for example, only optical means for orientation. When configuring the positioning aid as a positioning fin, physical contacting of the bone is desirable, however. Said positioning aid/positioning fin 4 is not absolutely necessary for particular embodiments of the invention.

The positioning fin 4 in any case perpendicularly projects from a horizontal web 5 in the direction of the mandible on a plane across the central component 2. There is an upper horizontal web 6 and a lower horizontal web 7. The positioning fin 4 projects from the lower horizontal web 7. In the present exemplary embodiment, it is plate-shaped, but it may as well be pin-shaped, for example having a circular, elliptic or polygonal cross-section.

At the distal ends 8 of the horizontal webs 5 the saw blade guide portions 3 are arranged in one piece and in one material in the form of blocks 9. In the blocks 9 saw slits 10 are provided. One saw slit 10 is provided for each saw blade guide portion 3.

The saw slit 10 is located between two vertically aligned bone separating tool contact faces 11 extending in parallel to each other.

At the front and/or at the bottom of the lower horizontal web 7 a marker 12 is formed as a centerline marker just as at the front and/or at the top of the upper horizontal web 6.

Instead of the centerline marker, also on the surface 13 of the positioning fin 4 facing the upper horizontal web 6 a ridge (not shown) extending in the longitudinal direction of the positioning fin 13, viz. from the lower horizontal web 7 toward the mandible, can be attached. Said ridge then may engage in a notch introduced to the bone and may act in a positioning manner.

One extension component 14 projects from both sides of the central component 2. The two extension components 14 are designed as integral parts of the central component 2 here. However, one extension component 14 or both extension components 14 may also be detachably coupled to the central component 2, viz. on the outside of each block 9. For this purpose, appropriate connecting points having coupling geometries such as projections and recesses, for example in the form of dovetail configurations can be designed, for example while forming a bottom and a stop.

In any case, each extension component 14 includes a base body 15 at each end of which an extra saw blade guide portion 16 is present. A setting mechanism 17 is used to safeguard displaceability of the extra saw blade guide portion 16 in the form of a further block from the base body 15. In the block-type extra saw blade guide portions 16, too, through-slits 18 are present which are configured similarly or identically to the slits/saw slits 10 in the saw blade guide portions 3.

A mandibular bearing block 19 having a slotted hole projects from the ends of the base body 15, e.g. in the area of the setting mechanism 17, or else from the extra saw blade guide portions 16. The slotted hole is not shown. In the exemplary embodiment presented here a slit extension 20 is used instead. The slotted hole may thus replace the slit extension 20, the longitudinal axis of the slotted hole configured as a through-hole is preferably orientated in the direction of the slit of the slit extension 20.

The setting mechanism includes a rod 21 on the front face/front surface 22 of which a corrugation 23 is provided. The rod 21 engages in a channel 24 of open design and is detachably held in position by a locking means 25 in the form of a set screw. In each extension component 14 there are at least two through-holes 26 for securing the mandibular resection template 1 by means of screws to the mandible not shown here.

In FIGS. 2 to 9, the mandibular resection template according to the invention is shown in different positions at a mandible 27.

In FIGS. 10 to 38, hereinafter the attention will increasingly be drawn to a fibular bone material resection and transfer template according to the invention and, resp., to the bone resected from a fibular bone and to bone pieces to be transplanted into the mandible.

Figure 10:
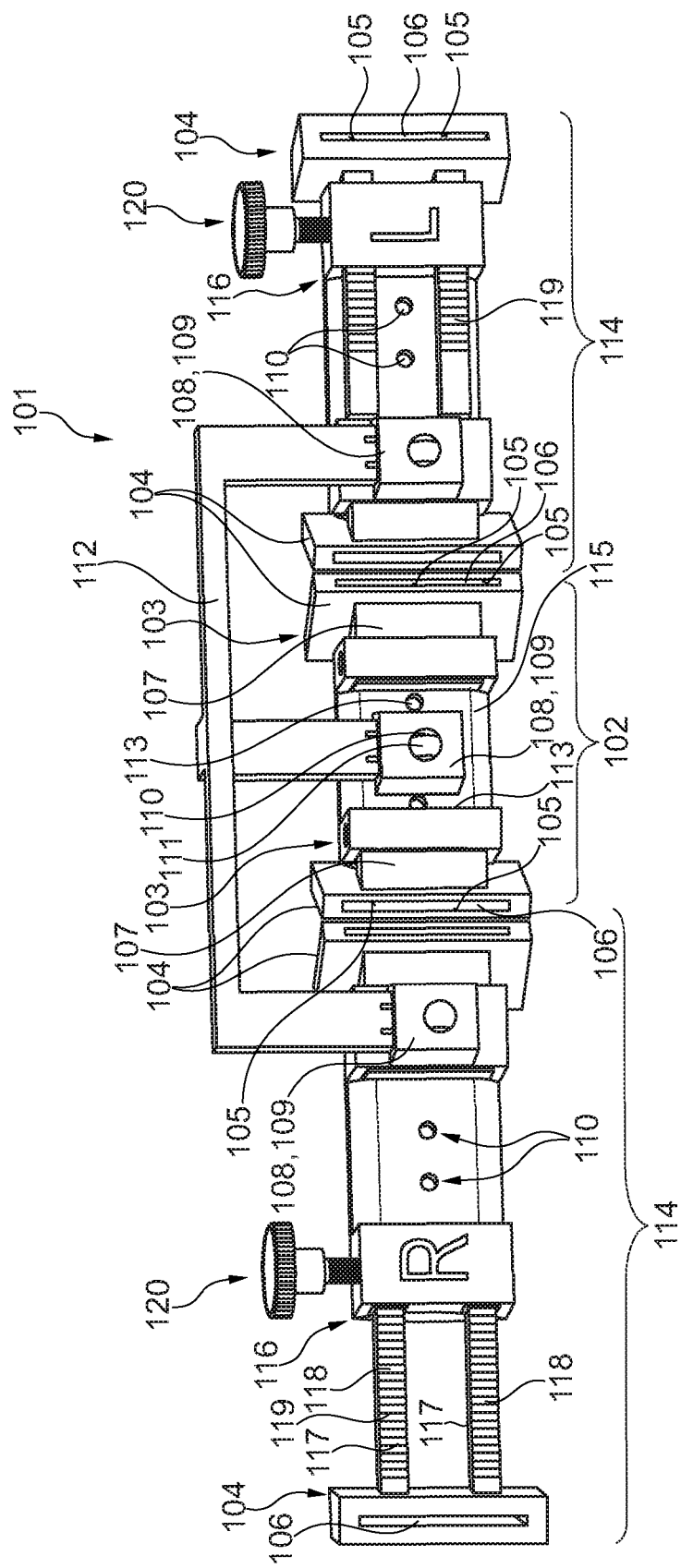
FIG. 10 shows a perspective view of a fibular bone material resection and transfer template according to the invention.

For example, in FIG. 10 a fibular bone material resection and transfer template 101 is illustrated. Said fibular bone material resection and transfer template 101 includes a central part 102. At each of the distal ends 103 thereof a bone separating tool guide portion 104 is present. Said bone separating tool guide portions 104 may be jaws or blocks and either may be connected integrally with the central part and, resp., a base body of the central part 102 or may be movably coupled thereto. At least one of the bone tool guide portions 104 should be supported so that it can be moved away, for example folded and/or removed and pushed close.

Each bone separating tool guide portion 104 includes a guide slit 106 between two vertical faces 105. Said guide slits 106 are open/permeable on the front and rear sides. Each guide slit 106 is completely surrounded by material except for the elongate openings in the front and rear sides. However, a guide slit 106 may be open at the bottom and/or at the top.

For displaceability of a bone separating tool guide portion 104 it is suggested to provide a beam 107. The beam 107 is movably supported in a guide path encompassing the same. A fixing screw not shown may be used for securing the beam 107.

In the middle of the central part 102 a bracket receiving device 108 is located. The bracket receiving device 108 is a clip 109 here and has a through-hole 110 into which a convex spring portion 111 of an auxiliary resection bracket 112 engages. On the left and on the right of the clip 109 a respective receiving hole 113 is provided to receive a bone screw by means of which attachment to a fibula bone can be implemented. The receiving holes 113 are configured in the form of bores.

On both sides of the central part 102 a respective supplementary component 114 adjoins. Between the supplementary component 114 a central body 115 of the central part 102 is thus arranged.

Each supplementary component 114 includes a further bone separating tool guide portion 104. Each of said bone separating tool guide portions 104 of the supplementary components 114 then is maintained to be displaceable via a displacing mechanism 116. Accordingly, two respective guide webs 117 are used both of which have ribs, notches or stops on their front side 118 so as to form a screening 119. In turn, bracket receiving devices 108 in the form of clips 109 are provided into which ends of the auxiliary resection bracket 112 engage. The connection between the auxiliary resection bracket 112 and the clips 109 is configured similarly or identically to the one described already before.

In each of the supplementary components 114 equally through-holes 110 are provided to enable fastening to bones via screws. The auxiliary resection bracket 112 is detachable for fixing the template. Set screws 120 are used for fixing the flexible slit.

While in FIG. 10 the fibular bone material resection and transfer template is shown substantially from the front, in FIG. 11 it is represented substantially from the rear, i.e. when viewed from the fibular bone. Hence the rear side is visible. The length of the supplementary components 114 preferably should be variable between 45.2 mm and 66.2 mm. The sequential length of the central part 102 preferably should be 30 mm and may be fixed.

Figure 15:
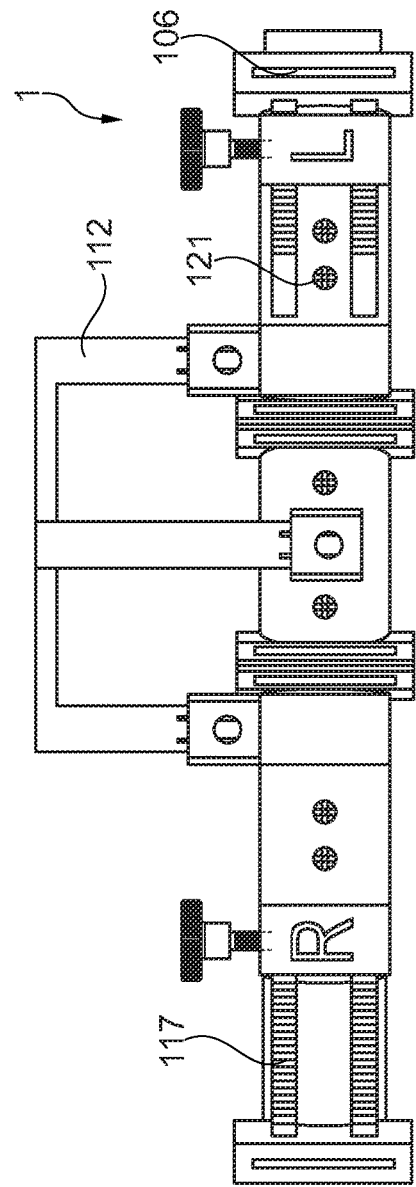
FIGS. 15 to 17 show a second embodiment of a fibular bone material resection and transfer template comprising a higher auxiliary resection bracket and blocks jointly receiving plural slits, with FIG. 15 corresponding to the view of FIG. 12 and FIG. 16 corresponding to a view of FIG. 13 as well as FIG. 17 corresponding to a view of FIG. 14.
Figure 16:
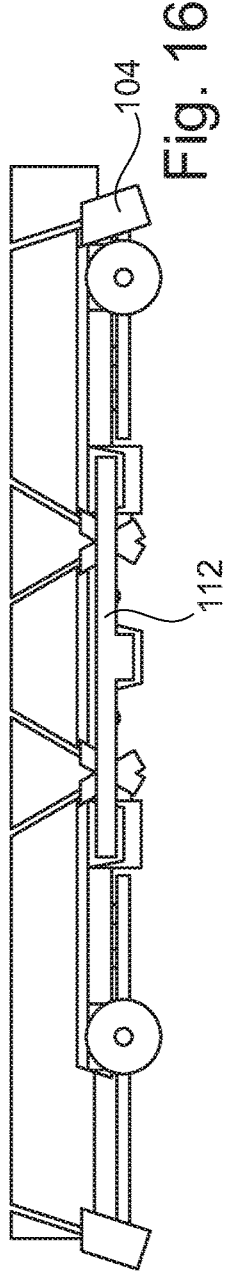
Figure 17:
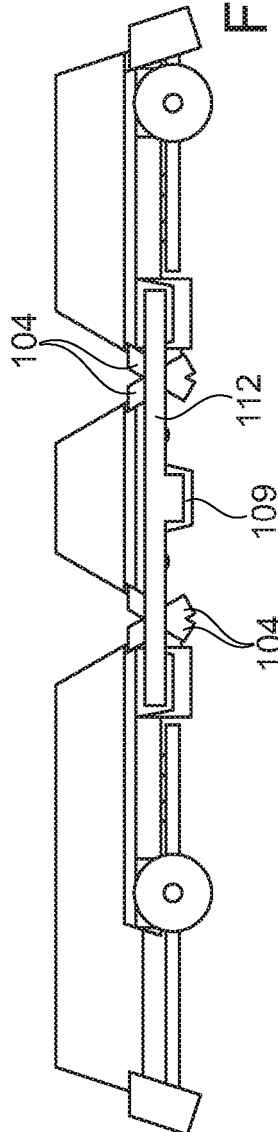
Figure 18:
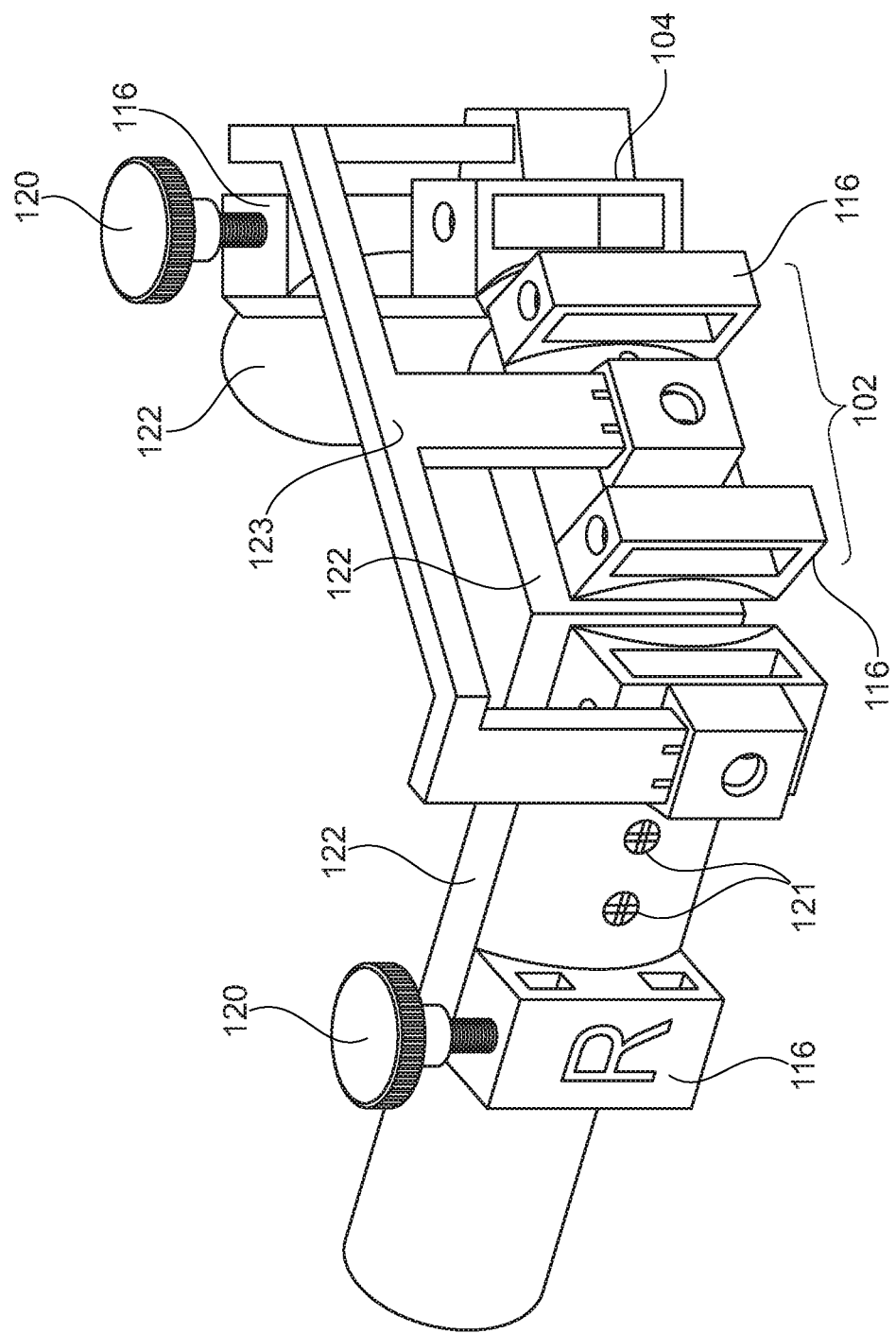
FIG. 18 shows the fibular bone material resection and transfer template according to the invention in a transfer position in which the bone pieces to be transplanted are transferred to the shape of the mandibular bone to be replaced or to be repaired.
Figure 25:
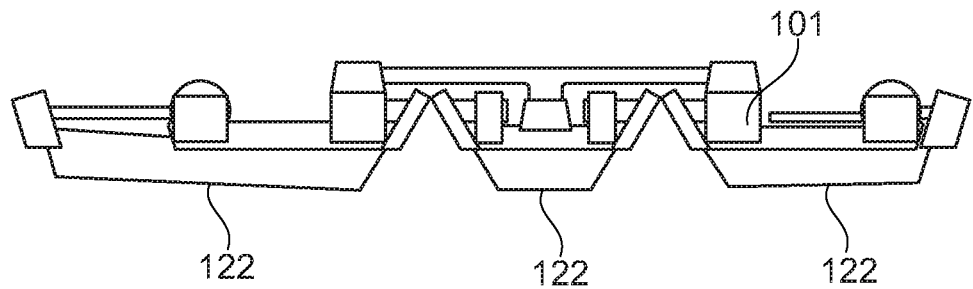
FIGS. 25 to 27 show the resected bone pieces at the attached fibular bone material resection and transfer template in forms of representation comparable to FIGS. 22 to 24, FIGS. 28 to 30 show the auxiliary implanting bracket geometrically modified vis-à-vis the first auxiliary resection bracket by means of which the resected bone pieces are brought into a shape similar to the mandible and thus are prepared for being transplanted.
Figure 26:
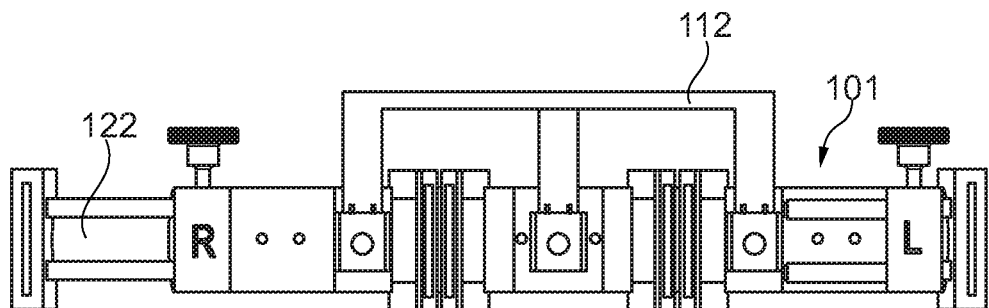
Figure 27:
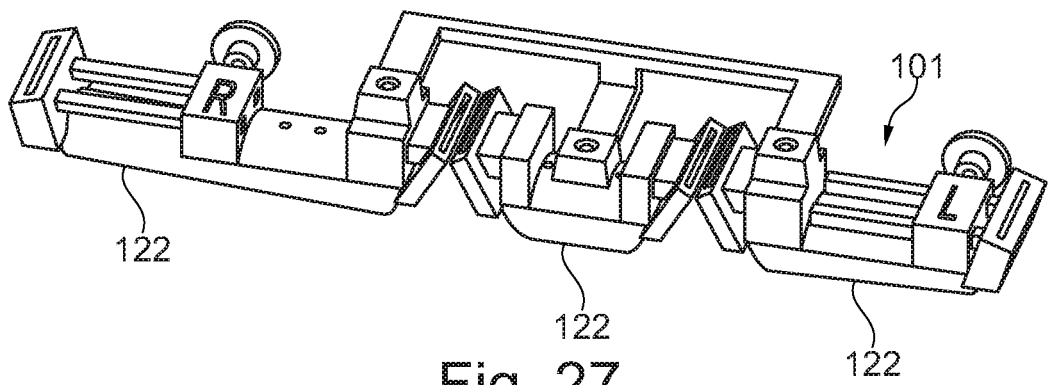
Figure 28:
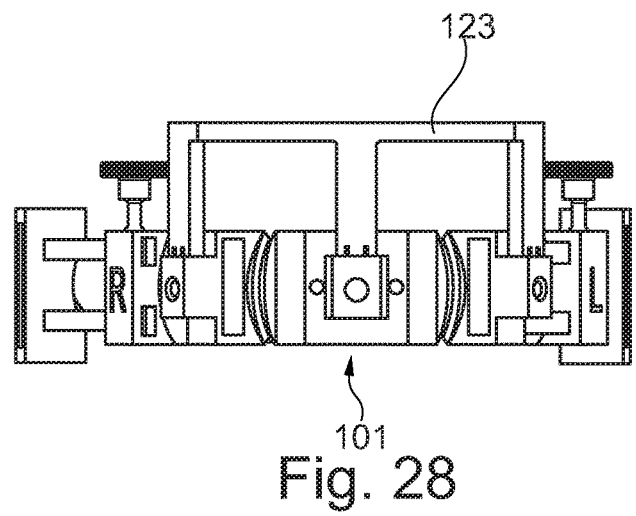
Figure 29:
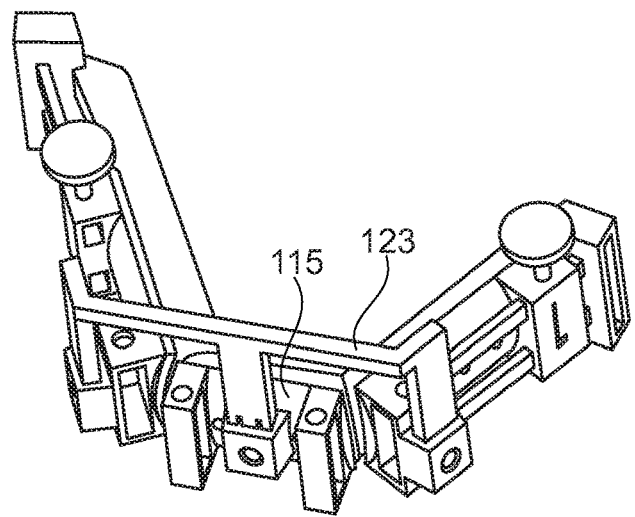
Figure 30:
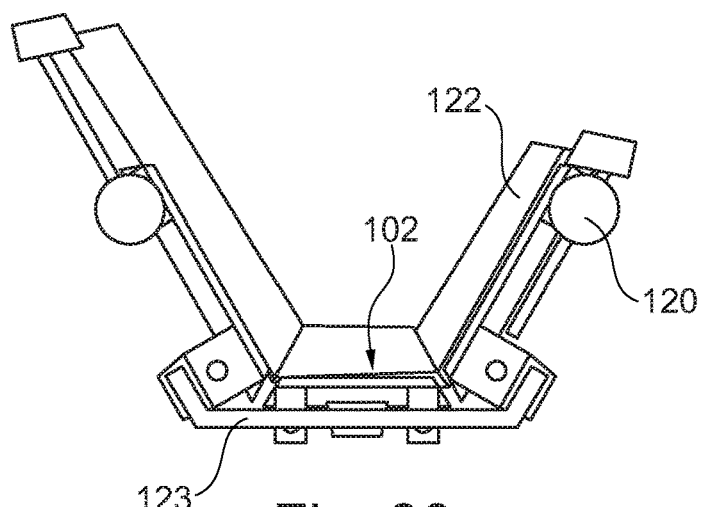
Figure 31:
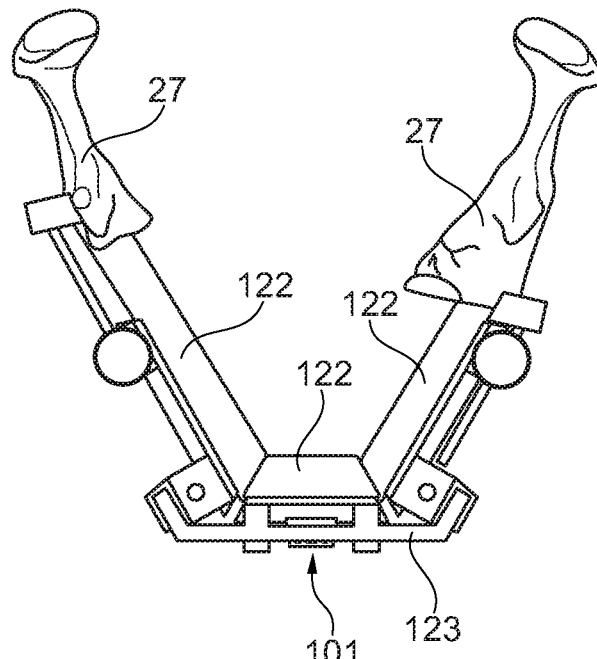
FIGS. 31 to 33 show the fibular bone pieces brought into position in the state inserted in the remaining mandible in a top view, a front view and a perspective view.
Figure 33:
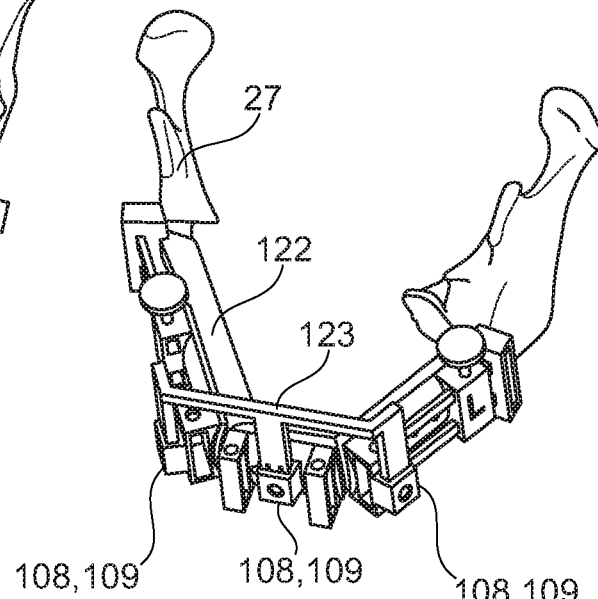
Figure 32:
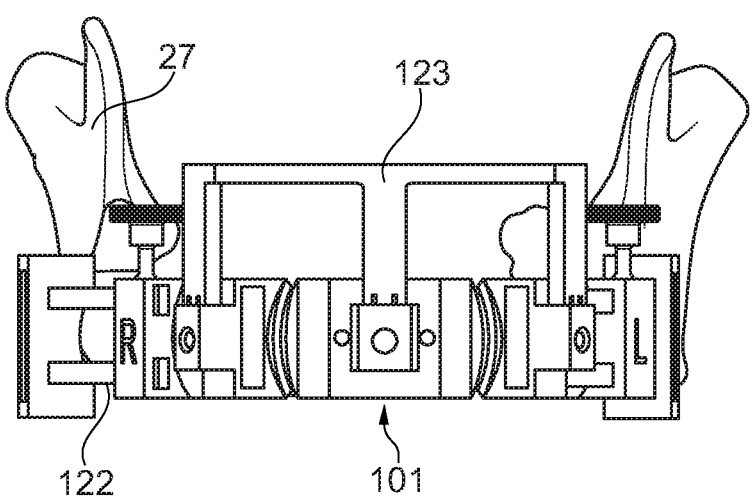

In FIGS. 12 and 15 already bone screws 121 are inserted so as to obtain, as in FIGS. 13 and 14 and 16 as well as 17, the fastening on parts of a fibular bone 122. In FIG. 18 an auxiliary implanting bracket 123 which is slightly different in geometry from the auxiliary resecting bracket 112 is used. The individual portions of the fibular bone 122 then are completely newly arranged, in the spatial position similarly as predefined by the mandibular resection template 1, preferably identically. The distally outermost bone separating tool guide portions 104 have been removed. This is also true for the bone separating tool guide portions 104 of the central part 102. The saw slits or guide slits 106 were removed so as to be able to set the segments "to be abutting".

The operation of attaching, cutting and resecting as well as subsequent assembling can be clearly inferred from FIGS. 19 to 38.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

LIST OF REFERENCE NUMERALS 1 mandibular resection template
2 central part/central component
3 separating tool guide portion/saw blade guide portion
4 positioning aid/positioning fin
5 horizontal web
6 upper horizontal web
7 lower horizontal web
8 distal end of horizontal web
9 block
10 saw slit
11 bone separating tool contact face
12 marker
13 surface of positioning fin
14 extension component
15 base body
16 extra saw blade guide portion
17 setting mechanism
18 through-slit
19 mandibular bearing block
20 slit extension
21 rod
22 front surface
23 corrugation
24 channel
25 locking means
26 through-hole
27 mandible
101 fibula bone material resection and transfer template
102 central part
103 end
104 bone separating tool guide portion
105 vertical face
106 guide slit
107 beam
108 bracket receiving device
109 clip
110 through-hole
111 spring portion 112 auxiliary resection bracket
113 receiving hole
114 supplementary component
115 central body
116 displacing mechanism
117 guide web
118 front side
119 screening
120 set screw
121 bone screw
122 fibular bone
123 auxiliary implanting bracket

We claim:

1. A mandibular resection template comprising: a central component which is prepared for attachment to a mandible or a maxilla, wherein at least two separating tool guide portions are present at the central component, and wherein a positioning aid is provided between the at least two separating tool guide portions in order to obtain a spatially correct orientation of the mandibular resection template with respect to the jawbone, wherein the central component is in the form of a frame having two horizontal webs, wherein on a front side and/or an upper side of at least one of the horizontal webs a center line marker is present.

2. The mandibular resection template according to claim 1, wherein the positioning aid is configured as a notch and bead combination, notch, bore, prism, color marker, pin, screw or navigation positioning and/or as a positioning fin prepared for entering into contact with a portion of a mandibular bone.

3. The mandibular resection template according to claim 1, wherein the positioning aid projects transversely from the central component.

4. The mandibular resection template according to claim 1, wherein the two horizontal webs are connected to each other at their distal ends via the two separating tool guide portions configured as saw blade guide portions.

5. The mandibular resection template according to claim 4, wherein the two separating tool guide portions and the two horizontal webs take a rectangular shape at least in a frontal projection.

6. The mandibular resection template according to claim 4, wherein the two horizontal webs and the two separating tool guide portions are configured as a uniform and/or one-piece/integral and/or single-material component.

7. The mandibular resection template according to claim 1, wherein either of the separating tool guide portions are in the form of a saw blade guide portion including a saw slit which is dimensioned to guide a bone separating tool.

8. The mandibular resection template according to claim 7, wherein on both sides of the saw slit a bone separating tool contact face parallel thereto is formed.

9. The mandibular resection template according to claim 7, wherein the saw slit protrudes completely through a material forming the same and, in addition, is configured in extension of its longitudinal extension to be open on one side or on two sides.

10. The mandibular resection template according to claim 9, wherein the material forming the saw slit is block-shaped and/or one of the horizontal webs is in the form of a rectangular beam.

* * * * *